United States Patent
Cruise et al.

(10) Patent No.: US 12,257,370 B2
(45) Date of Patent: Mar. 25, 2025

(54) COATINGS FOR MEDICAL DEVICES

(71) Applicant: MicroVention, Inc., Aliso Viejo, CA (US)

(72) Inventors: Gregory M. Cruise, Rancho Santa Margarita, CA (US); Steve Plotkin, Beaumont, CA (US); Petr Vasek, Costa Mesa, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 1260 days.

(21) Appl. No.: 16/938,571

(22) Filed: Jul. 24, 2020

(65) Prior Publication Data

US 2021/0023276 A1    Jan. 28, 2021

Related U.S. Application Data

(60) Provisional application No. 62/879,287, filed on Jul. 26, 2019.

(51) Int. Cl.
   *A61L 29/08* (2006.01)
   *A61L 29/04* (2006.01)
   *A61M 25/00* (2006.01)
   *A61B 5/15* (2006.01)

(52) U.S. Cl.
   CPC .......... *A61L 29/085* (2013.01); *A61L 29/049* (2013.01); *A61B 5/150992* (2013.01); *A61L 2400/10* (2013.01); *A61M 25/0045* (2013.01)

(58) Field of Classification Search
   None
   See application file for complete search history.

(56) References Cited

U.S. PATENT DOCUMENTS

| | | | |
|---|---|---|---|
| 4,378,430 A | 3/1983 | Modrovich | |
| 4,459,317 A | 7/1984 | Lambert | |
| 4,465,770 A | 8/1984 | Modrovich | |
| 4,487,808 A | 12/1984 | Lambert | |
| 4,842,597 A * | 6/1989 | Brook | A61L 33/064 604/372 |
| 5,077,352 A | 12/1991 | Elton | |
| 5,114,783 A | 5/1992 | Hodnett, III | |
| 5,164,321 A | 11/1992 | Zdunek et al. | |
| 5,225,267 A | 7/1993 | Ochi et al. | |
| 5,281,468 A | 1/1994 | Klier et al. | |
| 5,545,208 A | 8/1996 | Wolff et al. | |
| 5,662,960 A | 9/1997 | Hostettler et al. | |
| 5,736,251 A | 4/1998 | Pinchuk | |
| 5,753,453 A | 5/1998 | Kwan | |
| 5,776,661 A | 7/1998 | Casaletto | |
| 5,804,299 A | 9/1998 | Nakata et al. | |
| 5,888,656 A | 3/1999 | Suzuki et al. | |
| 6,030,656 A | 2/2000 | Hostettler et al. | |
| 6,083,257 A | 7/2000 | Taylor | |
| 6,099,562 A | 8/2000 | Ding | |
| 6,673,453 B2 | 1/2004 | Beavers | |
| 6,706,408 B2 | 3/2004 | Jelle | |
| 6,803,069 B2 | 10/2004 | Patnaik et al. | |
| 7,008,979 B2 | 3/2006 | Schottman | |
| 7,264,859 B2 | 9/2007 | Rouns | |
| 7,494,687 B2 | 2/2009 | Cox | |
| 7,544,381 B2 | 6/2009 | Kangas | |
| 7,544,673 B2 | 6/2009 | DeWitt | |
| 7,553,546 B1 | 6/2009 | Tan | |
| 7,770,828 B2 | 8/2010 | Matsumoto et al. | |
| 8,263,720 B1 | 9/2012 | Salamone et al. | |
| 10,543,299 B2 | 1/2020 | Baldwin et al. | |
| 11,188,869 B2 | 11/2021 | Subramaniam et al. | |
| 11,278,649 B2 | 3/2022 | Baldwin et al. | |
| 11,744,925 B2 | 9/2023 | Cruise et al. | |
| 11,783,278 B2 | 10/2023 | Subramaniam et al. | |
| 11,827,862 B2 | 11/2023 | Rangwala et al. | |
| 2001/0021745 A1 * | 9/2001 | Laginess | C08G 18/3821 528/61 |
| 2002/0082679 A1 | 6/2002 | Sirhan | |
| 2002/0094322 A1 | 7/2002 | Lawson et al. | |
| 2002/0120033 A1 | 8/2002 | Keogh et al. | |
| 2003/0069647 A1 | 4/2003 | Desmond | |
| 2003/0187493 A1 | 10/2003 | Campbell et al. | |
| 2005/0055044 A1 | 3/2005 | Kangas | |
| 2006/0052757 A1 | 3/2006 | Fischer, Jr. et al. | |
| 2006/0121217 A1 | 6/2006 | Childs et al. | |
| 2006/0251795 A1 | 11/2006 | Kobrin et al. | |
| 2007/0154703 A1 | 7/2007 | Waller et al. | |
| 2009/0076596 A1 | 3/2009 | Adden et al. | |
| 2009/0112239 A1 | 4/2009 | To | |
| 2009/0297607 A1 | 12/2009 | Wang et al. | |
| 2009/0324666 A1 | 12/2009 | Krongauz et al. | |

(Continued)

FOREIGN PATENT DOCUMENTS

| | | |
|---|---|---|
| CN | 101622019 B | 1/2015 |
| WO | 2013/130850 A1 | 9/2013 |

(Continued)

OTHER PUBLICATIONS

Vijay et al., Acrylic acid-methyl methacrylate copolymer for oral prolonged drug release, J Mater Sci: Mater Med, 2010, 21, 2583-2592. (Year: 2010).*
Zhu et al., Polysulfone hemodiafiltration membranes with enhanced anti-fouling and hemocompatibility modified by poly(vinyl pyrrolidone) via in situ cross-linked polymerization, Material Science and Engineering C 74, 2017, 159-166. (Year: 2017).*
International Search Report and Written Opinion, mailed Oct. 26, 2020, for International Application No. PCT/US2020/043528 filed on Jul. 24, 2020.
Office Action, dated Aug. 31, 2023, for Chinese Patent Application No. 202080053658.2 (Original and Translation enclosed).
Bruice, Acid-Base Properties of Amino Acids. Organic Chemistry, Fifth Edition (textbook), Pearson Education Inc., p. 1025 (2007).

(Continued)

*Primary Examiner* — Francisco W Tschen
(74) *Attorney, Agent, or Firm* — K&L Gates LLP; Brian J. Novak; Benjamin D. Heuberger

(57) ABSTRACT

Lubricious or hemocompatible coatings for medical devices are described.

7 Claims, No Drawings

(56) References Cited

U.S. PATENT DOCUMENTS

| | | |
|---|---|---|
| 2010/0105799 A1 | 4/2010 | Rudd |
| 2010/0113871 A1 | 5/2010 | Dias et al. |
| 2010/0198168 A1 | 8/2010 | Rooijmans |
| 2010/0236684 A1 | 9/2010 | Garlough |
| 2011/0000788 A1 | 1/2011 | Deschamps |
| 2011/0117282 A1 | 5/2011 | Bernard |
| 2011/0151000 A1 | 6/2011 | Schultz et al. |
| 2011/0160382 A1 | 6/2011 | Pacetti |
| 2011/0183867 A1 | 7/2011 | Davies et al. |
| 2013/0243936 A1 | 9/2013 | Garretson et al. |
| 2013/0261566 A1 | 10/2013 | Lockwood et al. |
| 2014/0011928 A1 | 1/2014 | Iwasawa et al. |
| 2018/0093019 A1 | 4/2018 | Baldwin et al. |
| 2018/0325649 A1 | 11/2018 | Wu et al. |
| 2019/0201589 A1* | 7/2019 | Farrell .................. A61L 29/143 |
| 2020/0157374 A1* | 5/2020 | Nakabayashi ....... C09D 133/08 |
| 2022/0162470 A1 | 5/2022 | Wu et al. |
| 2023/0303743 A1 | 9/2023 | Cruise et al. |
| 2023/0381380 A1 | 11/2023 | Cruise et al. |
| 2024/0084210 A1 | 3/2024 | Rangwala et al. |

FOREIGN PATENT DOCUMENTS

| | | |
|---|---|---|
| WO | 2017/158148 A1 | 9/2017 |
| WO | 2018/209306 A1 | 11/2018 |
| WO | 2020/159881 A1 | 8/2020 |
| WO | 2021/021642 A1 | 2/2021 |
| WO | 2022/026689 A1 | 2/2022 |

OTHER PUBLICATIONS

Weber, Use of ionic and zwitterionic (Tris/Bis Tris and HEPES) buffers in studies on hemoglobin function. J. Appl. Physiol., 72(4):1611-1615 (1992).

Tsai et al., Dopamine-assisted immobilzation of poly(ethylene imine) based polymers for control of cell-surface interactions. Acta Biomaterialia 7, pp. 2518-2525 (2011).

Nagaoka et al., "Low friction hydrophilic surface for medical devices," Journal of Bioactive and Compatible Polymers, 5:212-226 (1990).

International Search Report and Written Opinion, dated May 30, 2013, for International Application No. PCT/US2013/028380 filed on Feb. 28, 2013.

International Search Report and Written Opinion, dated Apr. 14, 2020, for International Application No. PCT/US2020/015240 filed on Jan. 27, 2020.

International Search Report and Written Opinion, dated Nov. 2, 2021, for International Application No. PCT/US2021/043677 filed on Jul. 29, 2021.

* cited by examiner

COATINGS FOR MEDICAL DEVICES

RELATED APPLICATIONS

This application claims priority of U.S. Provisional Patent Application No. 62/879,287, filed Jul. 26, 2019, the entire content of which is incorporated herein by reference.

FIELD

Described herein are coatings for medical devices and methods of applying those coatings.

BACKGROUND

Catheters and microcatheters are tubular devices that are used to conduct diagnostic and therapeutic endovascular interventions. One purpose of catheters is to maintain long-term vascular access, for example, to permit blood draws or delivery of medications into the bloodstream. Catheters are often formed of thermoplastic polymers that have high frictional forces. These high frictional forces make vascular navigation difficult. Additionally, long term blood contact results in thrombosis, protein adsorption, and platelet activation. Providing a coated catheter or microcatheter with a lubricious coating as described herein would be useful and beneficial.

SUMMARY

The herein described coatings can be applied to medical devices such as medical devices that can be subjected to human tissues. In some embodiments, the coatings can be applied to medical devices can are used inside vessels or other lumens. In some embodiments, the vessels can be blood vessels. In some embodiments, the medical devices can be catheters or microcatheters. In some embodiments, the medical devises can be central venous catheters or dialysis catheters.

The coatings can be synthetic and durable and lubricious. In some embodiments, the coatings can be ultra-violet (UV) cured. Lubricious coatings can reduce and/or minimize frictional forces between a medical device, such as a catheter or microcatheter, and a vessel wall, thereby enhancing trackability of the medical device throughout the vasculature. Lubricious coatings can also reduce or minimize thrombosis, protein adsorption, or platelet activation triggered as a result of vascular contact with a medical device. The surfaces of catheters are modified with lubricious coatings to reduce the frictional forces and enhance the ability of the catheter to be advanced through tortuous and distal vasculature.

In some embodiments, the herein described coatings can include two layers, a base coat and a top coat. The base coat functions as a tie layer between the catheter's thermoplastic polymer surface and the top coat. The base coat is designed to adhere to the catheter and provide binding sites for the attachment of the top coat. The top coat is designed to adhere to the base coat and provide lubricity to reduce the frictional forces when the catheter is moved in the vasculature, and to enhance the hemocompatibility of the catheter in a vascular environment. The top coat can be any synthetic or naturally occurring small molecule, protein, glycosaminoglycan, or polymer.

In some embodiments, the coatings can include: a base coat including a copolymer of a first tetrahydrofurfuryl acrylate monomer and a second monomer including a functional group amenable to further derivatization and plurality of reactive moieties, and a top coat containing more than two reactive moieties per molecule.

Methods of coating a thermoplastic surface, such as a catheter or microcatheter surface, are also described. The methods can include: applying a base coat including a copolymer of a first tetrahydrofurfuryl acrylate monomer and a second monomer to the thermoplastic surface, and applying a top coat to the base coat, wherein the top coat includes a top coat polymer containing more than two reactive moieties per molecule.

Methods of administering a catheter to a subject in need thereof, wherein the catheter is as described herein, are also described. The methods can include inserting the catheter into the subject, and removing the catheter at a time that is about 10% to about 200% longer than the time of removal of a catheter without a coating described herein.

Methods of providing vascular access to a subject in need thereof, comprising inserting a catheter described herein into the subject, are also described.

Methods of drawing bodily fluid (e.g., blood) from a subject in need thereof, comprising inserting a catheter described herein into the subject and drawing the bodily fluid from the subject, are also described. The methods can include repeatedly or continuously drawing the bodily fluid without repeatedly inserting the catheter.

Methods of administering an agent (e.g., a therapeutic or diagnostic agent) to a subject in need thereof, comprising inserting a catheter described herein into the subject and administering the agent to the subject via the catheter, are also described. The methods can include repeatedly or continuously administering the agent without repeatedly inserting the catheter.

The methods described herein can include inserting the catheter into the subject, and removing the catheter at a time that is about 10% to about 200% longer (e.g., about 10%, about 20%, about 30%, about 40%, about 50%, about 75%, about 100%, about 125%, about 150%, about 175%, or about 200%) than the time of removal of a catheter without a coating described herein.

DETAILED DESCRIPTION

Described herein are coatings for medical devices. In some embodiments, the coatings can increase the lubricity of the medical device. In some embodiments, the coatings can increase the hemocompatibility of the medical device. These medical devices can include catheters and microcatheters that are formed at least partially of thermoplastic polymers/materials. The thermoplastic polymers can include, but are not limited to, poly(amides), poly(ethylene terephthalate), poly(urethanes), poly(ether sulfones), poly (carbonates), poly(vinyl chloride), copolymers thereof, and derivatives thereof.

These thermoplastic polymers can have high frictional forces. These high frictional forces make vascular navigation difficult. Thus, the herein described coatings can increase lubricity of the thermoplastic polymer surfaces. Additionally, these thermoplastic polymers can lack or have low hemocompatibility. Thus, the herein described coatings can increase hemocompatibility of the thermoplastic polymer surfaces. In some embodiments, the coatings can include a base coat and a top coat. The base coat functions as a tie layer between the catheter's thermoplastic polymer and the top coat. The base coat is designed to adhere to the catheter and provide binding sites for the attachment of the top coat. The top coat is designed to adhere to the base coat and provide lubricity to reduce the frictional forces when the catheter is moved in the vasculature, or to increase hemocompatibility when placed in the vasculature.

In some embodiments, the base coat includes a polymer that is a copolymer of a first tetrahydrofurfuryl acrylate monomer and at least one other monomer with functional groups capable of further chemical reaction such as hydroxyl, amine, and carboxylic acid groups. In some embodiments, the at least one other monomer including hydroxyl groups can be hydroxyethyl methacrylate, hydroxyethyl acrylate, hydroxypropyl acrylate, hydroxypropyl methacrylate, hydroxybutyl acrylate, hydroxybutyl methacrylate, combinations thereof, and derivatives thereof. In some embodiments, the at least one other monomer including amine groups can be N-(3-aminopropyl) methacrylamide, 2-aminoethyl methacrylate, 2-aminoethyl methacrylamide, combinations thereof, and derivatives thereof. In some embodiments, the at least one other monomer including carboxylic acids can be acrylic acid, methacrylic acid, beta-carboxyethyl acrylate, combinations thereof, and derivatives thereof.

To prepare the base coat copolymer, the two or more monomers and optionally an initiator can be dissolved in a solvent. The solvent can be any solvent that dissolves the two or more monomers and the optional initiator. Solvents can include benzene, toluene, xylene, dimethylformamide, dimethyl sulfoxide, dioxane, 2-methyltetrahydrofuran, anisole, benzonitrile, chlorinated aromatic solvents, diisopropyl ether, diglyme, butanol, and combinations thereof.

Initiators can be used to start the polymerization of the monomers in the solution. The polymerization can be initiated by reduction-oxidation, radiation, heat, or any other method known in the art. Radiation cross-linking of the monomers in solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the monomers in solution.

In some embodiments, the initiator is azobisisobutyronitrile (AIBN) or a water soluble AIBN derivative (e.g., 2,2'-azobis(2-methylpropionamidine) dihydrochloride), or 4,4'-azobis(4-cyanopentanoic acid). Other initiators can include N,N,N',N'-tetramethylethylenediamine, ammonium persulfate, benzoyl peroxides, and combinations thereof, including azobisisobutyronitriles.

In some embodiments, the initiator concentration can be from about 0.25% w/w to about 2% w/w of the mass of the monomers in solution.

In some embodiments, the polymerization reaction can be performed at elevated temperatures, such as in the range from about 65° C. to about 85° C.

In some embodiments, after the polymerization is completed, the copolymer can be recovered by precipitation in a non-solvent and dried under vacuum.

In some embodiments, the resulting copolymer can have a molecular weight between about 15,000 g/mole and about 150,000 g/mole or between 25,000 g/mole to 100,000 g/mole. This molecular weight can be derived by gel permeation chromatography with polystyrene standards.

Following polymerization, reactive groups, such as acrylates and/or methacrylates, can be added to the copolymer via the hydroxyl, amine, and/or carboxylic acid groups of the second or more monomers. In some embodiments, the derivatization compound is a hetero-bifunctional compound. One moiety reacts with the hydroxyl, amine, and/or carboxylic acid groups of the copolymer. The other moiety is an acrylate or methacrylate group. Suitable derivatization compounds include 2-isocyanatoethyl acrylate, 2-isocyanatoethyl methacrylate, acrylic acid N-hydroxysuccinimide ester, methacrylic acid N-hydroxysuccinimide ester, heterobifunctional poly(ethylene glycol) with acrylate and isocyanate groups, combinations thereof, and derivatives thereof.

To prepare the derivatized copolymer, the copolymer, and derivatization compound, and optionally any catalyst, can be dissolved in a solvent. In some embodiments, any solvent that dissolves the components can be used. Solvents can include dimethyl formamide, dimethyl sulfoxide, toluene, acetone, acetonitrile, N,N-dimethylacetamide, N-methyl-2-pyrrolidone, and combinations thereof.

When reacting a derivatization with a nucleophilic group of the base coat copolymer, the molar equivalent of derivatization agent can range from about 5% to about 80% or about 10% to about 50% of the available nucleophilic groups. This level of derivatization corresponds to a range of 4 to 50 reactive groups per molecule. Further, in some embodiments, a Lewis base can be added of as a catalyst. Lewis bases can include triethylamine and pyridine. The Lewis base can be provided at a concentration of about 1% to about 10% of the moles of the derivatization compound added.

The reaction can proceed at elevated temperature, such as about 45° C. to form the base coat. After the derivatization is complete, the completed, decorated copolymer can be recovered by precipitation in a non-solvent and dried under vacuum.

The top coat can be formed on top of the base coat (e.g., the base coat can form a layer between a surface of the medical device and the top coat). The top coat polymer can include a hemocompatible small molecule, protein, polysaccharide, glycosaminoglycan, or polymer that is derivatized with polymerizable groups. The top coat polymer can be any naturally-occurring or synthetic polymer, derivatives thereof and combinations thereof. In some embodiments, the top coat polymer is, at least, to some degree, soluble in water.

The structure of the top coat polymer can be linear or branched, including graft, star, comb, brush, and dendrimer structures.

The top coat may include albumin, heparin, phosphorylcholine, poly(alkoxyalkyl (meth)acrylate), zwitterionic polymers, nitric oxide releasing polymers, extremely hydrophilic polymers, or extremely hydrophobic polymers.

Albumin is a protein found in blood and generally adsorbs on the surface of a foreign material, including catheters and microcatheters. Albumin does not have receptors to bind platelets, and when used as a coating material may block platelet interactions with surfaces. Albumin comprises nucleophilic amino acids, such as lysine and serine, permitting the derivatization and coating processes described herein.

Heparin is a polysaccharide that inactivates thrombin and inhibits blood coagulation. Heparin, when used a surface treatment, may decrease platelet adhesion and protein adsorption in medical devices. Heparin comprises carboxylic and hydroxyl groups in its structure, permitting the derivatization and coating processes described herein.

In addition to naturally occurring compounds, synthetic copolymers can be synthesized to create top coats to increase hemocompatibility.

In some embodiments, a first component of the copolymer is a compound to increase the hemocompatibility of the medical device (e.g., catheter or microcatheter) surface.

A second component can include a polymerizable acrylate or methacrylate as well as an amine, carboxylic acid, or hydroxyl group. Monomers containing amines include 3-aminopropyl methacrylamide, 2-aminoethyl methacrylate, N-(3-methylpyridine) acrylamide, 2-(N,N-dimethylamino) ethyl methacrylate, 2-(N,N-dimethylamino)ethyl acrylate, 2-(tert-butylamino)ethyl methacrylate, methacryloyl-L-lysine, N-(2-(4-aminophenyl)ethyl)acrylamide, N-(4-aminobenzyl)acrylamide, or N-(2-(4-imidazolyl)ethyl)acrylamide, derivatives thereof, or combinations thereof. Monomers containing carboxylic acids include acrylic acid, methacrylic acid, derivatives thereof, or combinations thereof. Monomers containing hydroxyl groups include 2-hydroxyethyl acrylate, 2-hydroxyethyl methacrylate, 2-hydroxypropyl acrylate, 4-hydroxybutyl acrylate, derivatives thereof, or combinations thereof.

To prepare the polymer, the two or more monomers and an initiator are dissolved in a solvent. Generally, any solvent that dissolves the two or more monomers and the initiator can be used. In some embodiments, the solvents include methanol/water, ethanol/water, isopropanol/water, dioxane/water, tetrahydrofuran/water, dimethylformamide/water, dimethylsulfoxide or water, and combinations thereof. With carboxylic acid and hydroxyl containing monomers, a wider range of solvents can be utilized, including toluene, xylene, dimethylsulfoxide, dioxane, tetrahydrofuran, methanol, ethanol, or dimethyl formamide.

Polymerization initiators can be used to initiate polymerization of the monomers in the solution. The polymerization can be initiated by reduction-oxidation, radiation, heat, or any other method known in the art. Radiation polymerization of the monomer solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the monomer solution. In some embodiments, the polymerization initiator is azobisisobutyronitrile (AIBN) or a water soluble AIBN derivative (e.g., 2,2'-azobis(2-methylpropionamidine) dihydrochloride), or 4,4'-azobis(4-cyanopentanoic acid). Other initiators useful according to the present description include N,N,N',N'-tetramethylethylenediamine, ammonium persulfate, benzoyl peroxides, or a combination thereof, including azobisisobutyronitriles. In some embodiments, concentrations of the initiator can range from 0.25% to 2% w/w of the mass of the monomers in solution. In some embodiments, the polymerization reaction can be performed at elevated temperatures, preferably in the range from 65 to 85° C. After the polymerization is completed, the polymer can be recovered by precipitation in a non-solvent and dried under vacuum. In some embodiments, the molecular weight of the copolymer can range from 500 amu to 100,000 amu, e.g., 1,000 amu to 40,000 amu.

One option for the first component to increase hemocompatibility is the use of alkoxyalkyl (meth)acrylates. Alkoxyalkyl (meth)acrylates can reduce protein adsorption, platelet adhesion, and conformational change of adsorbed proteins. In some embodiments, the alkoxyalkyl (meth)acrylate is 2-methoxyethylacrylate. In some embodiments, the alkoxyalkyl (meth)acrylate monomer can be represented by Formula (I):

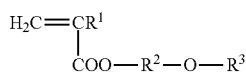

(I)

wherein
R$^1$ is a hydrogen atom or methyl group,
R$^2$ is an alkylene group with 1 to 4 carbons, and
R$^3$ is an alkylene group with 1 to 4 carbons.

In some embodiments, the first monomer is methoxyethyl acrylate, where R$^1$ is a hydrogen atom, R$^2$ is an ethyl group, and R$^3$ is a methyl group.

In some embodiments, the first component is a zwitterionic monomer, i.e. a monomer containing an equal number of positive and negative charges to have overall neutral charge. These compounds are hemocompatible due to their similarities in structure to the polar head groups of phospholipids that comprise the cell membrane. Additionally, due to the charges, zwitterionic compounds can tightly bind water and reduce protein conformation change.

In some embodiments, the zwitterionic monomer is 2-methacryloyloxyethyl phosphorylcholine:

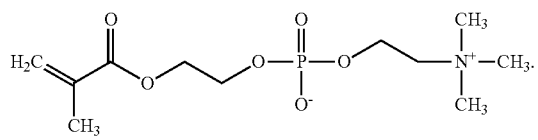 [SMILES: C=C(C)C(=O)OCCOP(=O)([O-])OCC[N+](C)(C)C]

In some embodiments, the zwitterionic monomer is a monomer synthesized from a betaine (i.e. carboxylbetaine, phosphobetaine, or sulfobetaine). An example of such a monomer is [2-(methacryloyloxy)ethyl]dimethyl-(3-sulfopropyl)ammonium hydroxide:

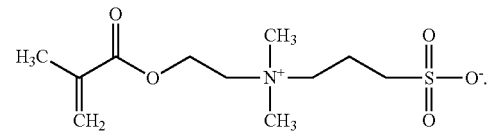

A third option for the first component is a monomer that releases nitric oxide. Nitric oxide inhibits platelets. The endothelial cell lining of arteries continually releases nitric oxide. A polymer that releases nitric oxide at a similar level may have similar hemocompatibility to that of the endothelial cell lining. Molecules containing (meth)acrylates and nitric oxide releasing chemistry such as diazeniumdiolate or S-nitrosothiol can be synthesized and subsequently polymerized into copolymers.

A fourth option for the first component is the use of very hydrophilic polymers/copolymers. Hydrophilic surfaces have been shown to reduce protein adsorption due to minimization of surface free energy. Hydrophilic monomers include acrylamide, vinyl alcohol, n-vinyl pyrrolidone, hydroxyethyl methacrylate, or poly(ethylene glycol).

Reactive groups, such as, but not limited to acrylates and/or methacrylates, can be added to the polymer via any convenient reactive moiety, such as hydroxyls, amines, or carboxylic acids, with a derivatization compound. In some embodiments, the derivatization compound can be a heterobifunctional compound. One moiety can react with the hydroxyl, amine, and/or carboxylic acid groups of the copolymer. The other moiety can be an acrylate or methacrylate group.

In some embodiments, the derivatization compound can include acryloyl chloride, methacryloyl chloride, 2-isocyanatoethyl acrylate, 2-isocyanatoethyl methacrylate, acrylic acid N-hydroxysuccinimide ester, methacrylic acid N-hydroxysuccinimide ester, hetero-bifunctional poly(ethylene glycol) with acrylate and isocyanate groups, combinations thereof, and derivatives thereof.

To prepare the derivatized polymer, the polymer, derivatization compound, and the optional catalyst are dissolved in a solvent. In some embodiments, any solvent that dissolves the top coat polymer, derivatization agent, and the optional catalyst can be used. Solvents can include aromatic and chlorinated solvents, including benzene, toluene, xylene, dichloromethane, chloroform, and combinations thereof.

When reacting a derivatization agent with a reactive moiety of the top coat polymer, the target derivatization corresponds to less than two groups per molecule. Additionally, in some embodiments, the derivitization can include addition of a Lewis base as a catalyst. In some embodiments, the Lewis base can be triethylamine and pyridine, in a concentration of about 1% to about 10% of the moles of the derivatization compound added.

In some embodiments, the derivitization reaction proceeds at room temperature.

After the derivatization is complete, an activated polymer can be recovered by precipitation in a non-solvent and dried under vacuum.

The base coat can be applied to a medical device surface, e.g., a thermoplastic material. The catheter is first cleaned by a solvent wipe to remove any gross contamination from its surface. In some embodiments, the catheter is wiped with a solvent. In some embodiments, any solvent can be used if it does not dissolve or degrade the thermoplastic material of the catheter. Solvents can include glycol ethers, methyl ethyl ketone, chlorinated solvents, tetrahydrofuran, hexane, ethyl acetate and acetone.

Following solvent cleaning, in some embodiments, the catheter shaft can be plasma treated to further clean its surface. In some embodiments, the catheter is not plasma treated. Plasmas derived from various gases can be used. In some embodiments, the plasma gases can be argon and oxygen. In some embodiments, both argon and oxygen plasmas can be used.

The base coat solution can include the solvent, base coat copolymer, an optional initiator, and an optional surfactant. Generally, any solvent or mixtures of solvents may be utilized, provided that the components can be dissolved into the solvent or solvent mixtures. Solvents can include water, alcohols, glycol ethers, aromatics, polar aprotic solvents, and combinations thereof. In some embodiments, the solvent can include methanol, ethanol, isopropyl alcohol, 2-ethoxy ethanol, propylene glycol monomethyl ether acetate, benzene, toluene, xylene, dimethyl formamide, dimethyl sulfoxide, and combinations thereof.

The base coat copolymer can be dissolved into the solvent at a concentration ranging from about 0.2% w/w to about 35% w/w, about 0.2% w/w to about 40% w/w, about 0.2% w/w to about 50% w/w, about 0.5% w/w to about 35% w/w, about 0.5% w/w to about 40% w/w, about 0.5% w/w to about 50% w/w, about 1% w/w to about 35% w/w, about 1 w/w to about 40% w/w, or about 1% w/w to about 50% w/w, depending on the desired viscosity of the basecoat solution. In some embodiments, the base coat copolymer concentration is about 15% w/w.

In some embodiments, if included, initiators can include Norrish Type I initiators, Norrish Type II initiators, and combinations thereof. Norrish Type I or free-radical photo-initiators can include benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, halogenated acetophenone derivatives, or a combination thereof. In some embodiments, Norrish Type I photoinitiators can include Irgacure 2959 (2-hydroxy-4'-(2-hydroxyethoxy)-2-methyl propiophenone), Irgacure 651 (benzildimethyl ketal or 2,2-dimethoxy-1,2-diphenylethanone, Ciba-Geigy), Irgacure 184 (1-hydroxy-cyclohexyl-phenyl ketone as the active component, Ciba-Geigy), Darocur 1173 (2-hydroxy-2-methyl-1-phenyl-propan-1-one as the active component, Ciba-Geigy), Irgacure 907 (2-methyl-1-[4-(methylthio)phenyl]-2-morpholino propan-1-one, Ciba-Geigy), Irgacure 369 (2-benzyl-2-dimethylamino-1-(4-morpholinophenyl)-butan-1-one as the active component, Ciba-Geigy), Esacure KIP 150 (poly{2-hydroxy-2-methyl-1-[4-(1-methylvinyl)phenyl]propan-1-one}, Fratelli Lamberti), Esacure KIP 100 F (blend of poly{2-hydroxy-2-methyl-1-[4-(1-methylvinyl)phenyl]propan-1-one} and 2-hydroxy-2-methyl-1-phenyl-propan-1-one, Fratelli Lamberti), Esacure KTO 46 (blend of poly {2-hydroxy-2-methyl-1-[4-(1-methylvinyl)phenyl]propan-1-one}, 2,4,6-trimethylbenzoyldiphenyl-phosphine oxide and methylbenzophenone derivatives, Fratelli Lamberti), acylphosphine oxides such as Lucirin TPO (2,4,6-trimethylbenzoyl diphenyl phosphine oxide, BASF), Irgacure 819 (bis(2,4,6-trimethylbenzoyl)-phenyl-phosphine-oxide, Ciba-Geigy), Irgacure 1700 (25:75% blend of bis(2,6-dimethoxybenzoyl)2,4,4-trimethyl-pentyl phosphine oxide and 2-hydroxy-2-methyl-1-phenyl-propan-1-one, Ciba-Geigy), or a combination thereof.

In some embodiments, mixtures of type I photo-initiators can be used.

Norrish Type II photo-initiators can also be used in the base coat formulation. These initiators can include aromatic ketones such as benzophenone, xanthone, derivatives of benzophenone (e.g. chlorobenzophenone), blends of benzophenone and benzophenone derivatives (e.g. Photocure 81, a 50/50 blend of 4-methyl-benzophenone and benzophenone), Michler's Ketone, Ethyl Michler's Ketone, thioxanthone and other xanthone derivatives like Quantacure ITX (isopropyl thioxanthone), benzil, anthraquinones (e.g. 2-ethyl anthraquinone), coumarin, or chemical derivatives or combinations of these photoinitiators.

In some embodiments, the base coat formulation can include combinations of Norrish Type I and Norrish Type II initiators.

The initiator concentration in the solvent can range from about 0.1% to about 6% w/w. In some embodiments, initiator concentration in the solvent can be about 0.6% w/w.

The base coat solution may also optionally include a surfactant. In some embodiments, any surfactant may be used. Surfactants can include sodium lauryl sulfate, Tween 20, Span 80, Triton X-100, Pluronic F68, Pluronic L-81, combinations thereof, and derivatives thereof. The optional surfactant can be dissolved into the selected solvent at a concentration ranging from about 0.1% w/w to about 15% w/w. In some embodiments, the surfactant concentration is about 0.8% w/w.

In some embodiments, to apply the base coat to a catheter, the length of the catheter desired to be coated is inserted into the base coat solution. The dip time, or amount of time the catheter spends in the base coat solution, ranges from about 0.2 to about 10 minutes, about 0.5 to about 10 minutes, about 2 to about 8 minutes, about 3 to about 6 minutes, or about 0.5 to about 8 minutes. In some embodiments, the dip time can be about 5 minutes.

In other embodiments, the base coat can be applied by spraying, brushing, spin coating, or the like, or a combination thereof including or not including dip coating.

In some embodiments, only portions of the catheter are coated. Therein portions of the catheter can be masked so that base coat is not applied to the masked regions.

After dip coating or otherwise applying the base coat, the catheter is exposed to ultraviolet radiation with a wavelength ranging from about 10 nm to about 400 nm, about 100 nm to about 400 nm, about 200 nm to about 400 nm, about 200 nm to about 300 nm, or about 300 nm to about 400 nm. Combinations of wavelengths in this range can also provide a suitable base coat. In one embodiment, ultraviolet radiation can be applied by a first wavelength between about 200 nm to about 300 nm and a second wavelength between about 300 nm to about 400 nm. In one embodiment, wavelengths can include 254 and 365 nm.

The cure time, or amount of time the catheter is exposed to ultraviolet radiation, ranges from about 0.5 to about 10 minutes, about 1 to about 10 minutes, about 1 to about 8 minutes, about 0.5 to about 6 minutes, about 1 to about 6 minutes, about 1 to about 3 minutes, or about 0.5 to about 30 minutes. In one embodiment, the cure time is about 2 minutes.

In some embodiments, the base coat application process is complete after the completion of the cure time.

The top coat can be applied to a completed base coat. The top coat solution can include the solvent, a top coat polymer, an optional initiator, and an optional surfactant. In some embodiments, any solvent or mixtures of solvents may be utilized, provided that the components can be dissolved into the solvent or solvent mixtures. Suitable solvents can include water, alcohols, glycol ethers, aromatics, polar aprotic solvents, and combinations thereof. In some embodiments, the solvent can include methanol, ethanol, isopropyl alcohol, 2-ethoxy ethanol, propylene glycol monomethyl ether acetate, benzene, toluene, xylene, dimethyl formamide, dimethyl sulfoxide, and combinations thereof.

The top coat polymer can be dissolved into the selected solvent at a concentration ranging from about 5% w/w to about 75% w/w, about 5% w/w to about 80% w/w, about 5% w/w to about 90% w/w, about 10% w/w to about 80% w/w, about 10% w/w to about 75% w/w, about 5% w/w to about 50% w/w, about 5% w/w to about 40% w/w, about 5% w/w to about 40% w/w, about 20% w/w to about 40% w/w, about 20% w/w to about 30% w/w, depending on the desired viscosity of the top coat solution. In one embodiment, the top coat polymer concentration is about 25% w/w.

The optional initiator can include Norrish Type I initiators, Norrish Type II initiators, and combinations thereof. Norrish Type I or free-radical photo-initiators can include benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, halogenated acetophenone derivatives, and the like. Norrish Type I photoinitiators can include Irgacure 2959 (2-hydroxy-4'-(2-hydroxyethoxy)-2-methyl propiophenone), Irgacure 651 (benzildimethyl ketal or 2,2-dimethoxy-1,2-diphenylethanone, Ciba-Geigy), Irgacure 184 (1-hydroxy-cyclohexyl-phenyl ketone as the active component, Ciba-Geigy), Darocur 1173 (2-hydroxy-2-methyl-1-phenylpropan-1-one as the active component, Ciba-Geigy), Irgacure 907 (2-methyl-1-[4-(methylthio)phenyl]-2-morpholino propan-1-one, Ciba-Geigy), Irgacure 369 (2-benzyl-2-dimethylamino-1-(4-morpholinophenyl)-butan-1-one as the active component, Ciba-Geigy), Esacure KIP 150 (poly {2-hydroxy-2-methyl-1-[4-(1-methylvinyl)phenyl]propan-1-one}, Fratelli Lamberti), Esacure KIP 100 F (blend of poly {2-hydroxy-2-methyl-1-[4-(1-methylvinyl)phenyl]propan-1-one} and 2-hydroxy-2-methyl-1-phenyl-propan-1-one, Fratelli Lamberti), Esacure KTO 46 (blend of poly {2-hydroxy-2-methyl-1-[4-(1-methylvinyl)phenyl]propan-1-one}, 2,4,6-trimethylbenzoyldiphenyl-phosphine oxide and methylbenzophenone derivatives, Fratelli Lamberti), acylphosphine oxides such as Lucirin TPO (2,4,6-trimethylbenzoyl diphenyl phosphine oxide, BASF), Irgacure 819 (bis(2,4,6-trimethylbenzoyl)-phenyl-phosphine-oxide, Ciba-Geigy), Irgacure 1700 (25:75% blend of bis(2,6-dimethoxybenzoyl)2,4,4-trimethyl-pentyl phosphine oxide and 2-hydroxy-2-methyl-1-phenyl-propan-1-one, Ciba-Geigy), and the like. Also, mixtures of type I photo-initiators can be used.

Norrish Type II photo-initiators that can be used include aromatic ketones such as benzophenone, xanthone, derivatives of benzophenone (e.g. chlorobenzophenone), blends of benzophenone and benzophenone derivatives (e.g. Photocure 81, a 50/50 blend of 4-methyl-benzophenone and benzophenone), Michler's Ketone, Ethyl Michler's Ketone, thioxanthone and other xanthone derivatives like Quantacure ITX (isopropyl thioxanthone), benzil, anthraquinones (e.g. 2-ethyl anthraquinone), coumarin, or chemical derivatives or combinations thereof.

In some embodiments, the top coat formulation can include combinations of Norrish Type I and Norrish Type II initiators.

The initiator concentration in the solvent can range from about 0.1% to about 6% w/w. In some embodiments, initiator concentration in the solvent can be about 0.3% w/w or about 0.5% w/w.

The top coat solution may also contain a surfactant. In some embodiments, any surfactant may be used. In some embodiments, surfactants can include sodium lauryl sulfate, Tween 20, Span 80, Triton X-100, Pluronic F68, Pluronic L-81, combinations thereof, and derivatives thereof. The optional surfactant can be dissolved into the selected solvent at a concentration ranging from about 0.1% w/w to about 5% w/w. In some embodiments, the surfactant concentration is about 0.6% w/w.

In some embodiments, to apply the top coat to a base coated catheter, the length of the catheter desired to be coated is inserted into the base coat solution. The dip time, or amount of time the catheter spends in the base coat solution, ranges from about 0.2 to about 20 minutes, about 0.5 to about 20 minutes, about 2 to about 15 minutes, about 3 to about 15 minutes, or about 8 to about 12 minutes. In some embodiments, the dip time can be about 10 minutes.

In other embodiments, the top coat can be applied by spraying, brushing, spin coating, or the like, or a combination thereof including or not including dip coating.

In some embodiments, only portions of the catheter are coated with the top coat. Therein portions of the catheter can be masked so that top coat is not applied to the masked regions.

After dip coating or otherwise applying the top coat, the catheter is exposed to ultraviolet radiation with a wavelength ranging from about 10 nm to about 400 nm, about 100 nm to about 400 nm, about 200 nm to about 400 nm, about 200 nm to about 300 nm, or about 300 nm to about 400 nm. Combinations of wavelengths in this range can also provide a suitable base coat. In one embodiment, ultraviolet radiation can be applied by a first wavelength between about 200 nm to about 300 nm and a second wavelength between about 300 nm to about 400 nm. In one embodiment, wavelengths can include 254 and 365 nm.

The top coat cure time, or amount of time the catheter is exposed to ultraviolet radiation, ranges from about 0.5 to about 4 minutes, about 1 to about 4 minutes, about 1 to about 3 minutes, about 0.5 to about 3 minutes, about 1 to about 5 minutes, about 0.5 to about 3 minutes, or about 0.5 to about 50 minutes. In one embodiment, the cure time is about 2 minutes.

The herein described coatings can provide a reduction in maximum dynamic friction force [gf] when compared to an uncoated device. In some embodiments, the coatings can reduce the maximum dynamic friction force by about 50%. In other embodiments, the coatings can reduce the maximum dynamic friction force by about 75%.

The herein described coatings can provide a reduction in average dynamic friction force at 60 mm displacement for 100 cycles [gf] when compared to an uncoated device. In some embodiments, the coatings can reduce the maximum dynamic friction force by about 50%. In other embodiments, the coatings can reduce the maximum dynamic friction force by about 75%.

The herein described coatings can provide an increase in lubricity when compared to an uncoated device. In some embodiments, the coatings can increase the lubricity by about 50%. In other embodiments, the coatings can increase the lubricity by about 75%.

Example 1

Preparation of a Base Coat Polymer

To a 1 L round bottom flask are added 80.0 g of tetrahydrofurfuryl acrylate, 18.5 g of 4-hydroxybuyl acrylate and 250 mL of toluene. The solution is de-gassed by purging argon gas through for 30 min. Then, 1.0 gram AIBN initiator is added, and the mixture is purged with argon for another 10 min. The flask is immersed in an 80° C. oil bath and reflux condenser with argon inlet attached. The mixture is heated for 16 hours under argon. The reaction is cooled down and precipitated with 1.2 L of cold MTBE, precipitated product; viscous polymer is collected and dried at vacuum. Typical yield is 85-95%.

The dried polymer is dissolved in dry DMF (200 mL, about 0.5 g/mL) and treated with 0.84 mL of triethylamine and 3.0 mL of isocyanatoethyl acrylate. The mixture is heated to 45° C. for 5 hrs. The polymer is precipitated out with 1.2 L of cold MTBE, washed 2×200 mL of MTBE and dried at high vacuum.

Example 2

Preparation of a Liquid Base Coat Solution

In an appropriate container, 6.75 g of polymer from Example 1 is dissolved in 45.0 mL of propylene glycol monomethyl ether acetate. Then, 0.34 g of Pluronic L-81 surfactant, 135 mg of benzophenone, and 135 mg 1-hydroxycyclohexyl phenyl ketone are added. Complete dissolution is achieved with shaking for 30 minutes produces a clear, homogeneous solution.

Example 3

Coating a Microcatheter with a Base Coat Solution

A 12" length (0.027" outer diameter) section of microcatheter with an external surface comprised of Grilamid L25 is prepared for coating by first inserting a tightly fitting stainless steel mandrel into the hollow inner lumen, then wiping the outer surface with acetone. The microcatheter section is then plasma treated with argon plasma (365 sccm, 300 watts, 500 mtorr) followed by oxygen plasma (120 sccm, 150 watts, 400 mtorr). The liquid base coat formulation prepared in Example 2 is transferred into a glass tube (12" length, 0.22" inner diameter) with a stoppered bottom. The microcatheter section is then placed into the coating solution in the glass tube and allowed to dwell for 5 minutes. The microcatheter section is removed and immediately cured by UV radiation (254 nm A, 1.3 J/cm$^2$ UV dose) over 2 minutes to polymerize the base coat onto the Grilamid substrate.

Example 4

Preparation of a top coat macromer

A mixture of 50 g (382 mmol) of methoxyethyl acrylate (MEA) and 13.8 g (96 mmol) of 4-hydroxybutyl acrylate (HBtAc) is dissolved in 250 mL of 1,4-Dioxane in a 1 L RB flask. AIBN (0.75 g) is added and dissolved by stirring, and a water-cooled condenser is attached. The flask is immersed into a pre-heated oil bath at 75° C. and the mixture is stirred for 16 hours. The reaction mixture is cooled and then poured into 1.2 L of MTBE. The precipitate is collected, washed two times with 200 mL of MTBE, separated and dried in vacuum.

The resulting MEA-co-HBtAc co-polymer is dissolved in anhydrous DMF (200 mL), and triethylamine (0.24 mL, 1.7 mmol) followed by 2-isocyanatoethyl acrylate (1.05 ml, 8.5 mmol) is added and reaction is stirred for 16 hours. The product is obtained by precipitation from 1.2 L of MTBE, washed two times with 200 mL of MTBE, separated and dried in vacuum.

Example 5

Preparation of a Top Coat Solution

In a container, 9.0 g of MEA-co-HBtAc top coat macromer prepared in Example 4 is dissolved in 45.0 mL of Dowanol with shaking. Then, 0.23 g of Pluronic L-81 surfactant, 90 mg of benzophenone, and 90 mg of 1-hydroxycyclohexyl phenyl ketone are added. Complete dissolution after shaking for 1 minute results in a clear, homogenous solution.

Example 6

Coating Microcatheter with a Top Coat Solution

The top coat solution prepared in Example 5 is transferred into a glass tube with a stoppered bottom and the microcatheter section with base coat from Example 3 is placed into the glass tube and allowed to dwell for 10 minutes in the top coat solution. The microcatheter section is then removed and immediately cured by UV radiation (254 nm λ, 1.3 J/cm$^2$ UV dose) over 2 minutes to polymerize the top coat onto the base coat.

The coating of example 6 compared to an uncoated sample illustrates an increase in hemocompatibility.

Although preferred embodiments have been described in this specification and the accompanying drawings, it will be appreciated that a number of variations and modifications may suggest themselves to those skilled in the pertinent arts. Thus, the scope of the present invention is not limited to the specific embodiments and examples described herein, but should be deemed to encompass alternative embodiments and equivalents.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:
1. A coated medical device comprising:
   a base coat including a copolymer of tetrahydrofurfuryl acrylate and 4-hydroxybutyl acrylate; and
   a top coat polymer containing more than two reactive moieties per molecule, wherein the top coat includes a hemocompatible copolymer of a first component and a second component,
   wherein the first component is selected from

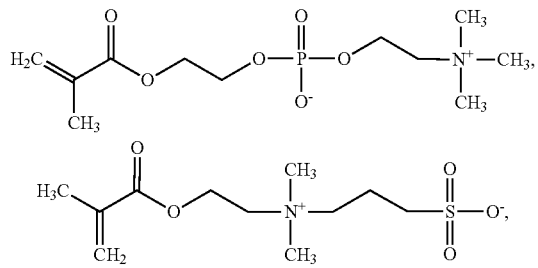

a (meth)acrylate monomer comprising a diazeniumdiolate or S-nitrosothiol moiety, a hydrophilic monomer, or methoxyethyl acrylate,
   wherein the hydrophilic monomer includes an acrylamide, vinyl alcohol, n-vinyl pyrrolidone, hydroxyethyl methacrylate, or poly(ethylene glycol) moiety.

2. The coated medical device of claim 1, wherein the copolymer has a molecular weight between about 15,000 g/mole and about 150,000 g/mole.

3. The coated medical device of claim 1, wherein the top coat is atop the base coat, or wherein the top coat is a hemocompatible top coat.

4. The coated medical device of claim 1, wherein the top coat polymer has a molecular weight between about 500 g/mole to about 100,000 g/mole.

5. The coated medical device of claim 1, wherein the top coat includes a copolymer of methoxyethyl acrylate and 4-hydroxybutyl acrylate.

6. The coated medical device of claim 1, wherein the second component is a monomer including an amine, carboxylic acid, or hydroxyl group.

7. The coated medical device of claim 6, wherein the second component is a monomer selected from:
   hydroxyethyl methacrylate, hydroxyethyl acrylate, hydroxypropyl acrylate, hydroxypropyl methacrylate, hydroxybutyl acrylate, hydroxybutyl methacrylate, or a combination thereof;

N-(3-aminopropyl) methacrylamide, 2-aminoethyl methacrylate, 2-aminoethyl methacrylamide, or a combination thereof; or
acrylic acid, methacrylic acid, beta-carboxyethyl acrylate, or a combination thereof.

\* \* \* \* \*